US00PP10035P

United States Patent [19]

Moore et al.

[11] Patent Number: Plant 10,035

[45] Date of Patent: Sep. 23, 1997

[54] BLUEBERRY—'OZARKBLUE'

[75] Inventors: James Norman Moore; John Reuben Clark, both of Fayetteville, Ark.

[73] Assignee: University of Arkansas, Fayetteville, Ark.

[21] Appl. No.: 607,904

[22] Filed: Feb. 26, 1996

[51] Int. Cl.[6] ..... A01H 5/00

[52] U.S. Cl. ..... Plt./33.1

[58] Field of Search ..... Plt./33.1

[56] References Cited

PUBLICATIONS

Clark, John R., et al., (1996) "'Ozarkblue' Southern Highbush Blueberry" *HartScience* 31(6):1043–1045.

*Primary Examiner*—James R. Feyrer

[57] ABSTRACT

Abstract of the Disclosure Description and specifications of a new and distinct blueberry variety which originated from seed produced by a hand pollinated cross of USDA Selection G-144 (non-patented) and Florida Selection 4–76 (non-patented) is provided. This new blueberry variety can be distinguished by its high productivity, large fruit size, late ripening, long ripening period, small pedicel scar, and good fruit color and firmness.

2 Drawing Sheets

SUMMARY OF THE INVENTION

The new and distinct variety of blueberry originated from a hand pollinated cross of USDA Selection G-144 (non-patented) ×Florida Selection 4–76 (non-patented) made in 1976 at the U.S. Department of Agriculture Research Station at Beltsville, Md. The parent plants used in this hybridization have not been named and released and are unavailable in commerce.

Plants and fruit of this new variety differ phenotypically from its parents. The new variety is earlier ripening, more productive, and possesses better fruit firmness but smaller fruit size than the parent USDA Selection G-144, and is later ripening, has larger fruit size, and is more flavorful than the parent Florida Selection 4–76. The new variety is an interspecific hybrid, derived from crossing three Vaccinium species. It is 13/16 *V. corymbosum* L., 2/16 *V.darrowi* Camp, and 1/16 *V. ashei* Reade. The new variety phenotypically exhibits plant and fruit characters predominately of the northern highbush blueberry, *Vaccinium corymbosum* L., but may possess genes for wider environmental and soil adaptability characteristic of its *V. darrowi* and *V. ashei* progenitors.

The seeds resulting from this controlled hybridization were germinated in a greenhouse at Beltsville, Md. in the fall of 1976. The resulting seedlings were shipped to Fayetteville, Ark. in March, 1977, potted and grown for one year in a lath house at the University of Arkansas. In March, 1978 the seedlings were planted in a field on the Arkansas Agricultural Experiment Station at Fayetteville, Ark. The seedlings fruited during the summer of 1980 and one, designated Ark. 109, was selected for its large fruit size, high productivity, and good fruit quality characteristics.

During 1981, the original plant selection was propagated asexually from hardwood stem cuttings, at the Arkansas Agricultural Experiment Station, Fayetteville, Ark. and larger test plantings were established with asexually multiplied plants at three additional locations in Ark.

The new variety has been asexually multiplied annually since 1981 by the use of both hardwood and softwood stem cuttings. During all asexual multiplication, the characteristics of the original plant have been maintained and no aberrant phenotypes have appeared.

Plants of the new variety are vigorous in growth and precocious in fruiting. Young plants of the new variety produce significantly higher yields following planting establishment than the Bluecrop variety, and its superior productivity is maintained consistently as the plants mature. Flower bud swell in spring is earlier than in the Bluecrop variety, but the bloom period coincides with Bluecrop. The new variety has not demonstrated susceptibility to either disease or winter cold in tests in Ark.

Fruit of the new variety begins ripening on average 9 days later than the Bluecrop variety, and produces ripe fruit an average of 7 to 14 days longer than the Bluecrop variety. Average ripening date is Jun. 14 in central Ark. Fruit yields are higher than the Bluecrop variety and most other varieties of highbush blueberry. Yields are consistent from year to year.

The fruit is globose in shape, light blue in color with whitish wax bloom on fruit surface and large in size (2.0–2.5 g). The fruit of the new variety is similar in color and size to the Bluecrop variety. The fruit is firm at maturity, rating more firm than the Bluecrop variety. The stem scar of the fruit is small and shallow, and is superior to the Bluecrop variety.

The fresh fruit rates good in flavor, being superior to the Bluecrop variety in most years. The flavor is sweet and mildly subacid, with a good blueberry aroma. Flavor is sweeter and more aromatic than the Bluecrop variety. The soluble solids concentration averages 11.5%. Seeds average 74/berry and are small and soft.

Fruit clusters are medium-large, racemose, and are borne on the terminal portions of canes. Flower fertility is high and clusters are well filled.

The new variety has been named the Ozarkblue cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the botanical and pomological characteristics of the subject blueberry. Color data are presented in Royal Horticultural Society Colour Chart designations and are supplemented, where possible, with readings from a Minolta Chroma Meter CR-200, version 3.0, which measures absolute chromaticity in tristimulus values Y, x, and y as determined by the Commission Internationale de l'Eclairage (CIE Yxy). Calibration was performed using a standard white plate supplied by the manufacturer.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant:

*Size.*—Similar to other northern highbush blueberry varieties.

*Growth.*—Vigorous, prolific cane production from crowns, canes bend with heavy fruit load.

*Productivity.*—High and for duration of 5 to 6 weeks; consistent from year to year.

*Cold hardiness.*—Hardy to–23° C., similar to Bluecrop.

*Canes.*—Erect, except canes may bend with heavy fruit load. Cane diameter: mature cane base 2.8 cm, midpoint 1.4 cm; one-year-old cane base 0.9 cm, midpoint 0.6 cm, terminus 0.2 cm. terminus 0.2 cm. Mature cane color (dormant): base, Greyed-Green (197A); midpoint, Greyed-Green (198A). One-year-old Cane Color (dormant): base, Greyed-Purple (183A); midpoint, Greyed-Purple (183B); terminus, Greyed-Red (182A).

*Disease resistance.*—Slightly susceptible to stem blight under field conditions; resistant to powdery mildew.

Foliage:

*Leaves.*—Medium. Mature leaf diameter 2.5 cm; length 5.4 cm. Mature leaf color: base abaxial-Green (138A) Y=19.13, x=0.3297, y=0.3797; base adaxial-Green (132A) Y=9.62, x=0.3356, y=0.4019; midpoint abaxial-Green (138A) Y=19.22, x=0.3279, y=0.3791; midpoint adaxial-Green (132A) Y=9.29, x=0.3338, y=0.4008; terminal abaxial-Green (138A) Y=19.08, x=0.3263, y=0.3776; terminal adaxial-Green (133A) Y=9.OO, x=0.3327, y=0.3990.

*Petiole length.*—0.37 cm.

*Leaf serration.*—None.

*Leaf pubesence.*—None.

Flowers:

*Date of flower bud swell (stage 2).*—Julian 53.

*Date of bloom.*—First — Julian 100; *full — Julian* 104.

*Blossom color.*—Red-Purple (65C) Y=64.36, x=0.3428, y=0.3627.

*Reproductive organs.*—Stamens — erect, numerous. Pistils—one per flower. Calyx—5 lobed. Pollen—normal and abundant.

*Number flowers per cluster.*—7 to 8.

*Number of petals per flower.*—5, fused to form a corolla tube.

Fruit:

*Maturity.*—Late, 9 days after Bluecrop. Average first ripe date is Jun. 14. Average period of ripening is Jun. 14 to Jul. 15.

*Size.*—Large, average 2.1g early season, 1.8g midseason, 1.3g late season. Diameter: Primary fruit at equator 1.58 cm, pole to pole 1.26 cm; secondary fruit equation 1.52 cm., pole to pole 1.20 cm; tertiary fruit equator 1.31 cm, pole to pole 1.03 cm.

*Shape.*—Globose, uniform.

*Color.*—Light blue with whitish wax bloom on surface: with bloom intact Violet-Blue (98A) Y=13.80, x=0.2834, y=0.2905; with bloom removed Blue (103A) Y=4.96, x=0.3103, y=0.3136.

*Pedicel scar size.*—Small, 1.46 mm.

*Seed size.*—Small, soft.

*Seed number.*—74/berry.

*Soluble solids.*—11.5%.

*pH.*—3.16.

*Acidity.*—1.13g/100 ml (as citric).

*Total anthocyanin (Abs. units/g fresh weight).*—108.

*Uses.*—Fresh and processed, jellies, jams, juice.

The variety: The most distinctive features of the variety are its high productivity, large fruit size, late ripening, long ripening period, small pedicel scar, and good fruit color and firmness.

We claim:

1. A new and distinct variety of blueberry plant, substantially as illustrated and described, characterized by its high productivity, large fruit size, late ripening, long ripening period, small pedicel scar, and good fruit color and firmness.

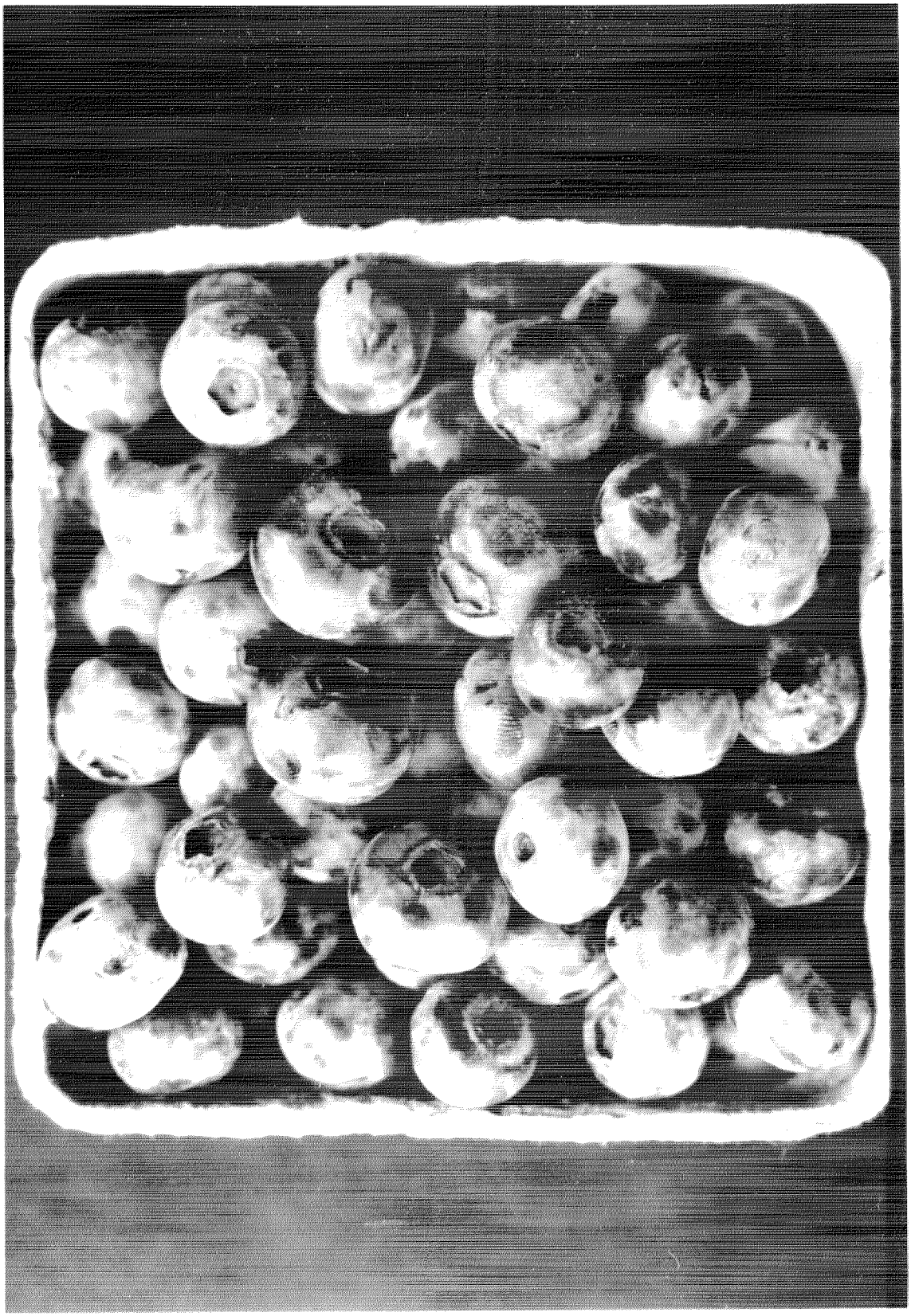

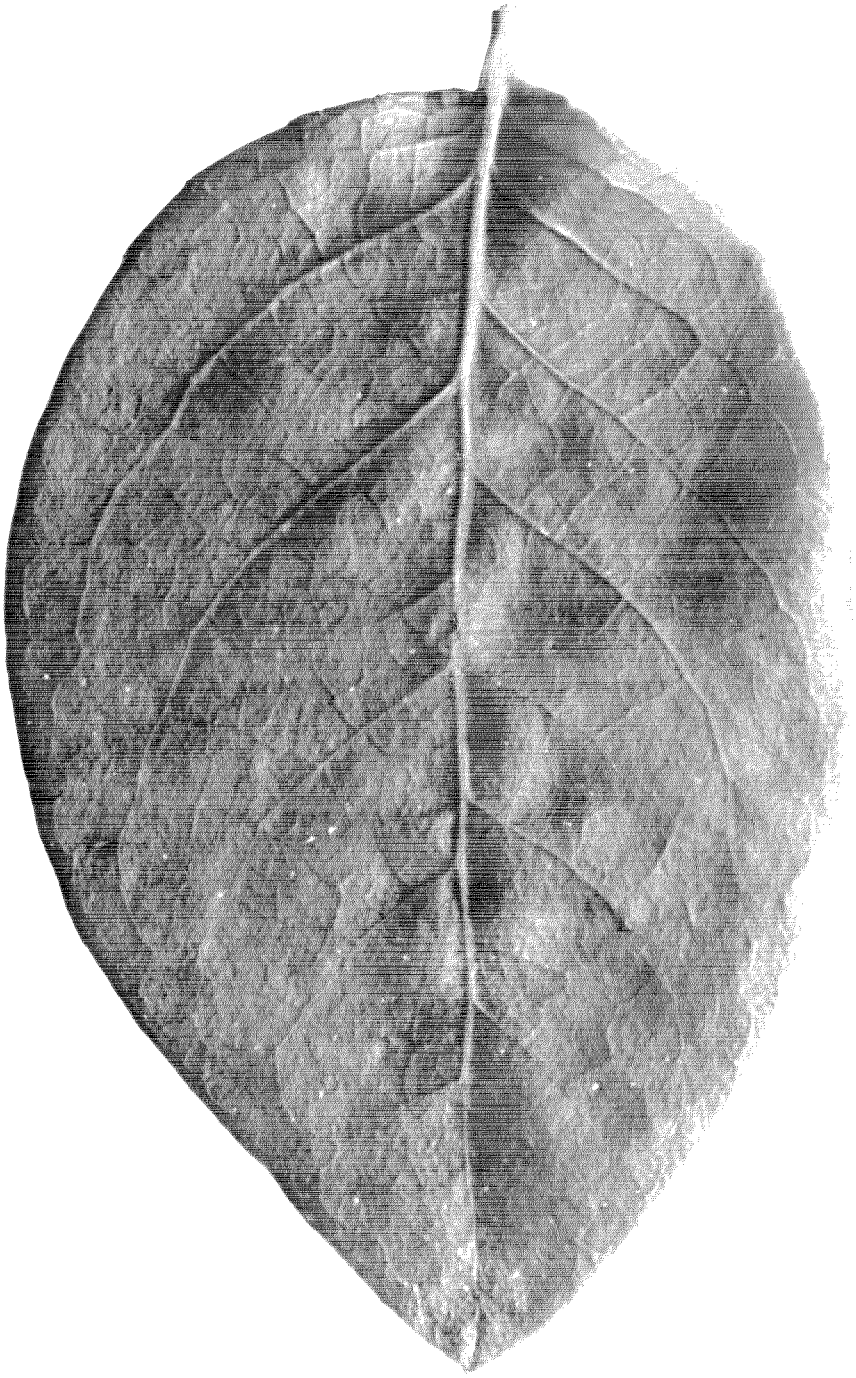

* * * * *